US00PP36985P2

(12) United States Plant Patent
Molnar et al.

(10) Patent No.: US PP36,985 P2
(45) Date of Patent: Sep. 30, 2025

(54) ***CORNUS* TREE NAMED 'Rutglow'**

(50) Latin Name: *Cornus kousa Buerger ex Miq.*
Varietal Denomination: Rutglow

(71) Applicant: Rutgers, The State University of New Jersey, Piscataway, NJ (US)

(72) Inventors: Thomas J. Molnar, East Brunswick, NJ (US); John M. Capik, Allenhurst, NJ (US)

(73) Assignee: Rutgers, the State University of New Jersey, New Brunswick, NJ (US)

( * ) Notice: Subject to any disclaimer, the term of this patent is extended or adjusted under 35 U.S.C. 154(b) by 0 days.

(21) Appl. No.: 19/038,365

(22) Filed: Jan. 27, 2025

(51) Int. Cl.
*A01H 5/00* (2018.01)
*A01H 6/00* (2018.01)

(52) U.S. Cl.
USPC ..... Plt./220
CPC ..... *A01H 6/00* (2018.05)

(58) Field of Classification Search
USPC ..... Plt./220
See application file for complete search history.

*Primary Examiner* — Susan McCormick Ewoldt
(74) *Attorney, Agent, or Firm* — Daugherty & Del Zoppo, LPA; Patrick J. Daugherty

(57) ABSTRACT

A new dogwood cultivar of *Cornus kousa* that is clearly distinguished by its floriferous display of symmetrical dark pink colored floral bracts and attractive dark-green foliage.

3 Drawing Sheets

Latin name of genus and species of the plant claimed: *Cornus kousa Buerger ex Miq.*

Variety denomination: 'Rutglow'.

BACKGROUND OF THE INVENTION

This new cultivar is the product of a long-standing program of hybridization and selection of big-bracted dogwoods. The purpose of the program was to develop new and superior cultivars of dogwoods expressing attractive, dark-pink colored floral bracts that are cold hardy in New Jersey and similar climates. The new cultivar 'Rutglow' originated from an open-pollination event of an unnamed pink-bracted *Cornus kousa* tree designated H3DR11P29 which is held in a germplasm collection of a horticultural farm located at 67 Ryders Lane, East Brunswick, Middlesex County, New Jersey, 08816 (hereinafter sometimes referred to as the "East Brunswick horticultural farm"). H3DR11P29 originated as an open pollinated seedling of the unreleased pink- bracted K187-44, which resulted from a cross of *Cornus kousa* 'Satomi' and *C. kousa* 'Benifuji' made in 1996 by Dr. Elwin Orton. The staminate (pollen) parent of 'Rutglow' is unknown. However, since dogwoods are self-incompatible and insect pollinated, the male parent is expected to be one of the adjacent dogwood trees of H3DR11P29 in a dedicated block of unreleased breeding selections planted in an isolated area of said East Brunswick horticultural farm specifically for cross pollination purposes. The progeny from which 'Rutglow' was selected were planted in the field in 2014 and evaluated for their phenotypic characteristics and assessed for value as commercial cultivars.

The inventors selected this specific seedling tree from a dedicated set of progeny trees grown in a cultivated area, and as a result, have in turn caused the same to be asexually reproduced by budding. The asexual reproduction and growth and selection of the new cultivar took place in East Brunswick, New Jersey. The claimed cultivar is stable and reproducible true-to-type in successive generations of asexual reproduction.

As will be demonstrated from the detailed description of the invention which appears hereinafter, the new cultivar is in fact outstanding and readily identified as being such. With the foregoing in mind, the description which follows will be understood as clearly defining the new cultivar, the desirable characteristics of which are the result of such a program as has been heretofore stated.

BRIEF SUMMARY OF THE INVENTION

The cultivar, designated here as 'Rutglow', originated in a cultivated field of a horticultural farm located at 67 Ryders Lane, East Brunswick, Middlesex County, New Jersey, 08816. Its specific location was row 5 in the H3G2 field of said East Brunswick horticultural farm and was evaluated under the identification code RUT 19-33. This seedling originated from an open-pollination event in 2013 of a *C. kousa* tree designated H3DR11P29 as part of a cross-pollination breeding block of unnamed dogwood selections located at said East Brunswick horticultural farm.

The seedling, which became this new cultivar, germinated in February 2014, was transplanted to progressively larger containers, and was planted in the field in September 2014. The cultivar was evaluated in place for its ornamental attributes and growth performance. After four years of floral bloom observations (2019-2022), it was asexually propagated by budding onto *C. kousa* seedling rootstock in August 2019 in Belvidere, Tennessee, and in Boring, Oregon, and was subsequently evaluated in those regions for propagation performance, powdery mildew response, growth habit and leaf quality, and floral bract characteristics. Five budded trees were returned to said East Brunswick horticultural farm in March 2021 from Belvidere, Tennessee, grown in containers and then field planted in September 2021 at said East Brunswick horticultural farm for observation along with the original tree.

The dogwood tree of the present invention is asexually propagated by grafting (usually chip-budding), by softwood cuttings, or via meristem culture (plant tissue culture). It is distinguished from patented and/or commercially available pink-bracted cultivars of *C. kousa, C. elwinortonii* (*C. kousa* x *C. nuttallii*), and *C. rutgersensis* (*C. florida* x *C. kousa*) hybrids in the following respects:

*Cornus kousa* 'Rutpink' Scarlet Fire® dogwood (US Plant Patent No.28, 311 P3) and 'Rutglow' both have dark-pink floral bracts of similar color but can be clearly differentiated by their shape and size. 'Rutpink' has distinctly long acuminate floral bracts whose length are nearly twice their width and with less than 10% overlapping of neighboring bracts at their base at anthesis. Their involucural spread of bottom and top bracts also averages around 13 cm. In contrast, the floral bracts of 'Rutglow' are much more rounded in shape whereas the individual bract length is only slightly longer than its width (width is 82-85% of the length) and there is more than 50% overlap at the base of the floral bract at anthesis. Their involucural spread averages around 10 cm. 'Rutglow' differs from its parent H3DR11P29 based on peak floral bract color and size. H3DR11P29 has bracts that are of a significantly lighter shade of pink at the time of anthesis represented by 36C and 36D Red Group ('Rutglow' is most closely represented by 52A and 52B Red Group). The involurval spread of H3DR11P29 is also larger, reaching on average 12.7 cm for the lower bracts and 12.5 cm for the upper, whereas 'Rutglow' averages 10.3 cm and 9.8 cm, respectively.

A group of five pink-bracted *C. kousa* cultivars currently available in the nursery trade includes 'Satomi' (also called 'Miss Satomi', not patented), 'Rosabella' (not patented), 'Rosea' (not patented), 'Schmred' (Heart Throb®, U.S. Plant Pat. No. 9,283 P), and 'Hanros' (Radiant Rose®, not patented). These cultivars are similar to one another in terms of floral bract shape and color. Trigiano et al. (2004) and Farr Moreau et al. (2024) using molecular genetic tools suggest they are very closely related or possibly even representations of the same cultivar but with different names. They differ from 'Rutglow' in both bract shape and color. Their mature floral bracts are ovate to obtuse in shape and are significantly longer than wide (Cappiello and Shadow, 2005), whereas 'Rutglow' has floral bracts that are much more rounded in shape with length only slightly larger than width, and with considerable overlap at their bases. Further, under New Jersey conditions in late May to early June, floral bract color in full sun at the time of anthesis for the five cultivars is generally light pink to a pinkish cream color with an uneven shading (typical base color of floral bracts is 36C and 36D Red Group with intermittent splotches of 49A Red Group and edges of floral bracts sometimes reaching 50B Red Group). In contrast, the floral bracts of 'Rutglow' remain uniform in color and are generally much darker pink with shades of red, with the color most closely represented by 52A and 52B Red Group.

*Cornus kousa* 'Benifuji' (U.S. Plant Pat. No. 8,676 P) differs from 'Rutglow' due to its smaller and much more narrow floral bracts that show little overlap of their bases at the time of anthesis. The floral bracts of 'Beni Fuji' are consistently lighter pink in New Jersey than 'Rutglow' although 'Benifuji' is generally darker pink than the five cultivars referenced above.

*Cornus elwinortonii* 'KN144-2' (Rosy Teacups®; U.S. Plant Pat. No. 26,211 P3), and interspecific hybrid with a lineage that contains both *C. kousa* and *C. nuttallii* differs from 'Rutglow' in the upward "cup-like" growth and development of its young floral bracts up until around the point of anthesis; 'Rutglow ''s young developing floral bracts do no stand upright like 'KN144-2'. The floral bracts of 'Rutglow' are also generally a darker shade of pink color at anthesis in New Jersey.

*Cornus rutgersensis* 'Rutgan' (Stellar Pink®; U.S. Plant Pat. No. 7,207 P) is an interspecific hybrid between *Cornus florida* and *Cornus kousa,* which has light-pink colored floral bracts that are nearly rounded to obovate in shape but with short, acute tips and tapered bases. 'Rutgan', in addition to having much lighter pink colored blooms, reaches anthesis around two weeks before 'Rutglow', indicative of its hybrid background, with an anthesis date between that of the earlier blooming *Cornus florida* and the later blooming (approximately 1 month) *Cornus kousa.* 'Rutgan' is also sterile, producing no mature fruit, whereas 'Rutglow' produces normal *C. kousa* fruit with fertile seeds.

'Rutglow' is associated with the trademark Eternal Scarlet™.

Further information relative to the Background of the Invention may be found at the following references. Mattera R., Molnar T., and Struwe L. (2015 ) "*Cornus* x *elwinortonii* and *Cornus* x *rutgersensis* (Cornaceae), new names for two artificially produced hybrids of big-bracted dogwoods." PhytoKeys 55:93-111. "Genetic diversity analysis of big bracted dogwood (*Cornus florida* and *C. kousa*) cultivars, interspecific hybrids, and wild-collected accessions using RADseq,". Moreau ELP, Medberry AN, Honig JA, and Molnar TJ (2024) PLOS ONE 19 (7): e0307326. "Genetic Profiling of Red-Bracted *Cornus kousa* Cultivars Indicates Significant Cultivar Synonomy," Trigiano R. H., Ament M. T., Windham M. T., and Moulton J. K., HortScience Jan. 1, 2004, Vol 39 Issue 3, pages 489-92; Online ISSN: 2327-9834.

BRIEF DESCRIPTION OF THE DRAWINGS

This new cultivar of dogwood is illustrated by the accompanying digital images that capture defining characteristics of the tree by the best possible color representation using digital color photography. All color references below are measured against The Royal Horticultural Society (R.H.S.) Colour Chart (1966). Colors are approximate as individual color depends on horticultural practices such as light level, temperature, and fertilization rate, among others.

DETAILED BOTANICAL DESCRIPTION

Figure 1:
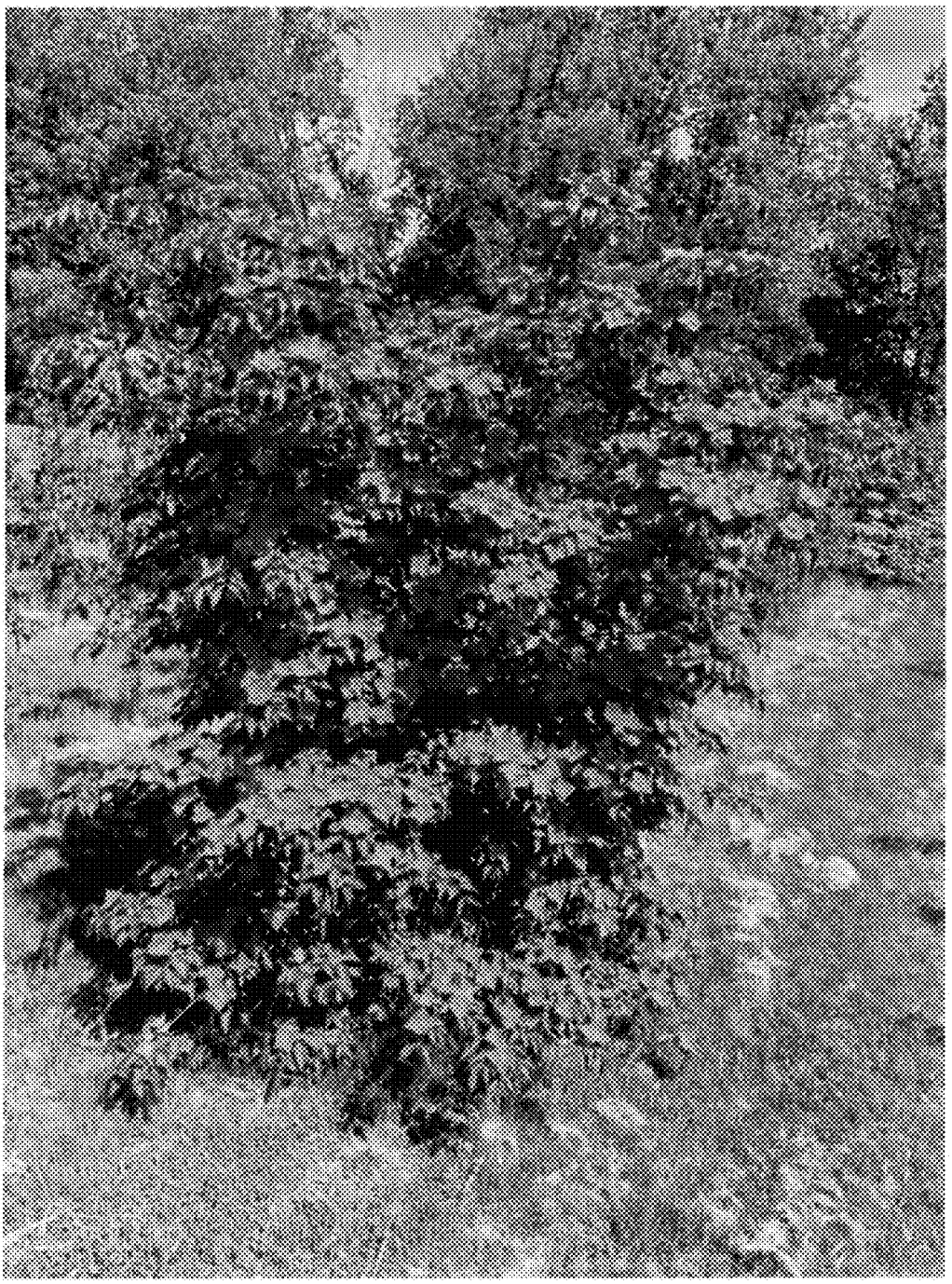
FIG. 1 shows an image of the original tree of 'Rutglow' at peak floral display at the age of 10 years. Picture taken May 27, 2023.
Figure 2:
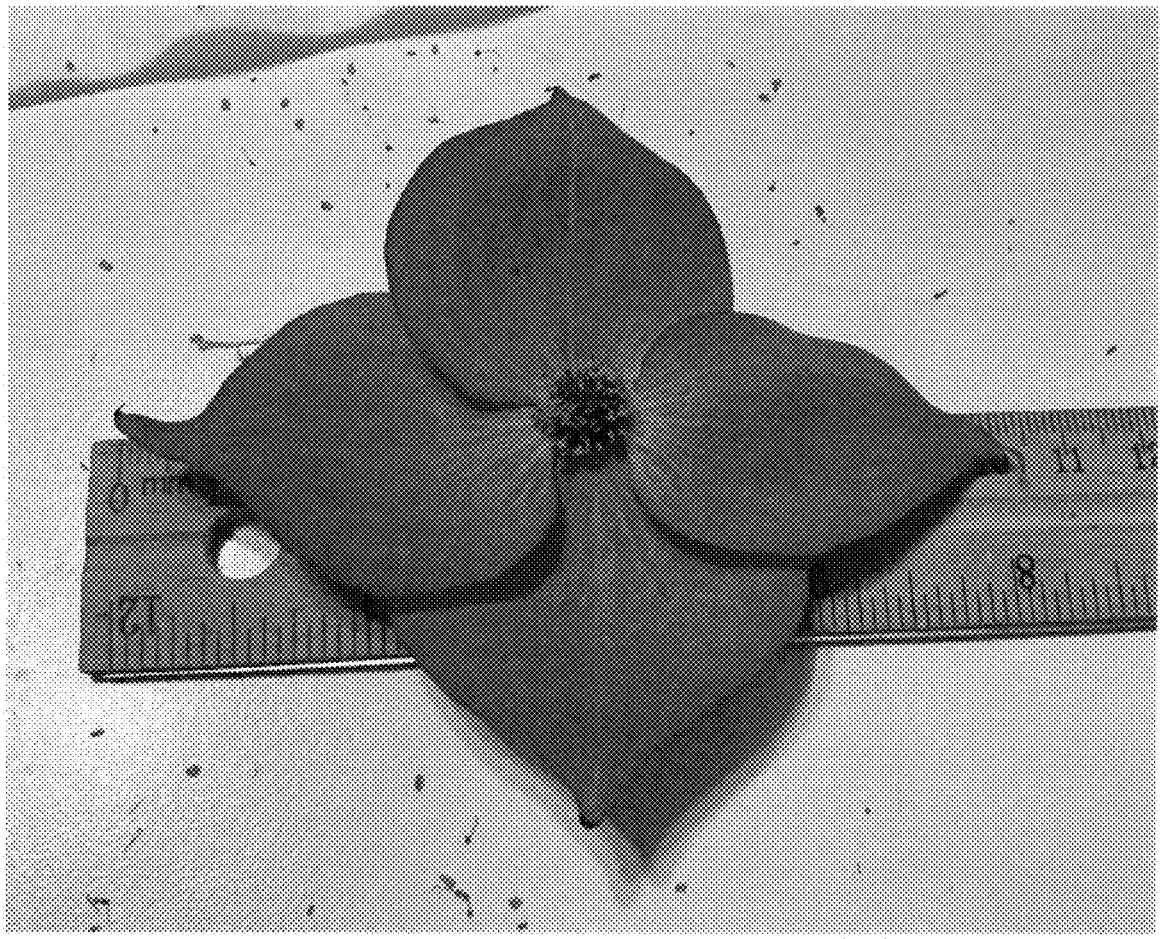
FIG. 2 shows a close-up view of a characteristic individual 'Rutglow' flower head at peak ornamental display. Note that the image shows the rounded floral bracts with acuminate tip and overlapped bases.
Figure 3:
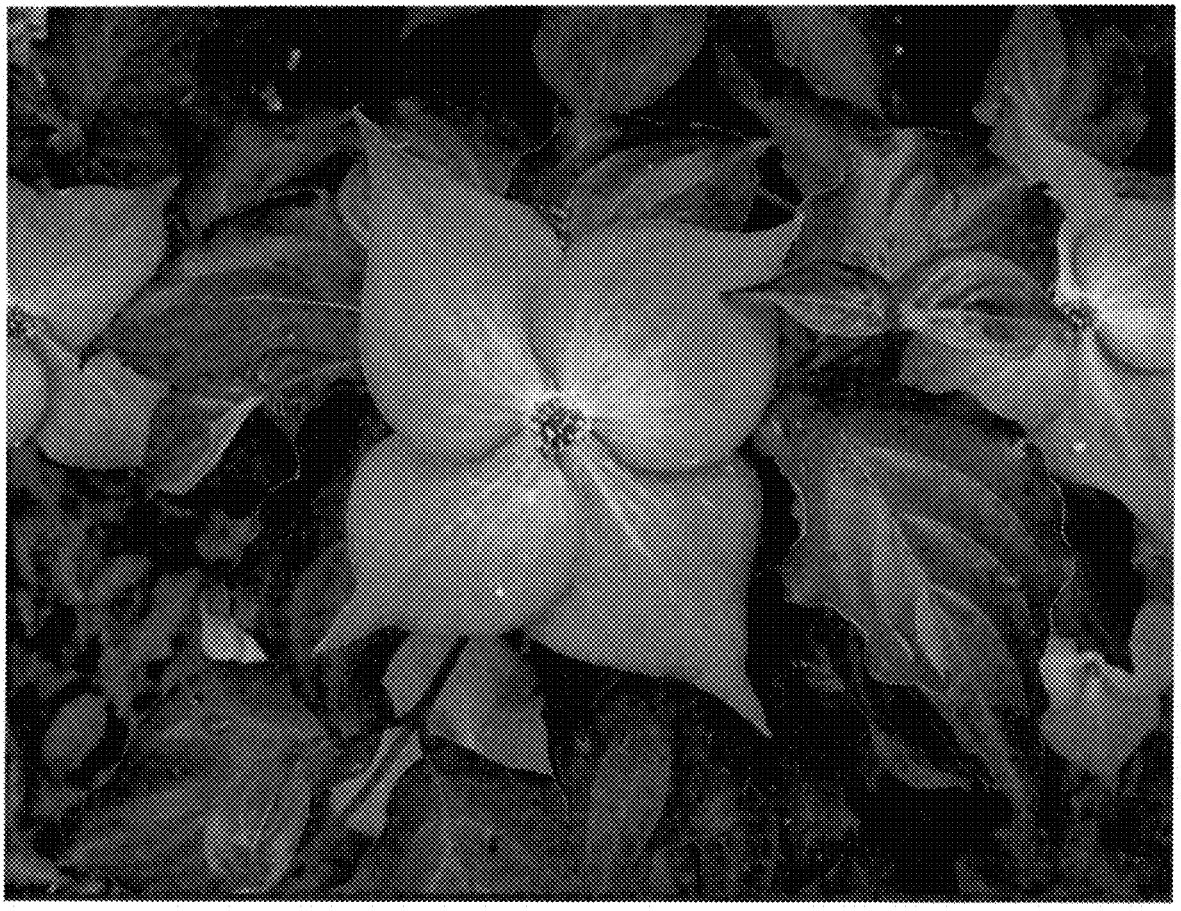
FIG. 3 shows the peak dark pink color of 'Rutglow' floral bracts and the dark green color of the leaves.

*Form.*—Tree. Growth habit: Dense tree branched to ground with semi upright branches which form a rounded head at maturity. Semi-vigorous, and slightly taller than wide.

*Height of original tree.*—3.2 meters at 11 years. Spread: 2.5 meters at 11 years. Plant vigor is similar to *Cornus kousa* species.

*Cold hardiness.*—The original seedling tree planted in 2014 and all grafted propagules, where hereinafter n=number of measurements, n=25 to date, since 2021 planting) have suffered no visible winter injury to vegetative or floral buds during the 11 winters under test in the field at East Brunswick, New Jersey, in 2023 USDA Plant Hardiness Map Zone 7b (0 degree to 5 degrees F.).

*Resistance to insects and diseases.*—No evidence of insect problems has been observed on the original seedling or its propagules in the years the plants have been under test in New Jersey, Tennessee, and Oregon. No sign or symptom of powdery mildew has been observed. No evidence of susceptibility to dogwood anthracnose or common dogwood borer has been presented.

*Trunk.*—Circumference of the trunk at 10 cm above the soil level was 45 cm after 11 growing seasons.

*Trunk texture.*—Smooth, although some parts sandpaper rough due to presence of lenticels.

*Color of bark on trunk and main scaffold branches.*—Closest to 197C and 197D Greyed Green Group. Younger stems (1 and 2 years) closest to 200C and 200B Brown Group. Three-year-old branches closest to 197C and 197D Greyed Green Group and textured due presence of lenticels (average 15-20 per $cm^2$). Lenticels are closest in color to 197D Greyed Green Group. Size of lenticels are 1.0-2.0 mm long by 0.3 mm-0.4 mm wide. Lenticels are present on younger stems but are less than 1.0 mm long, same color.

*Branches.*—Crotch angle on primary branches from trunk range from 45-60 degrees; subsequent smaller branches originating on the primary branches range from 45-50 degrees.

Foliage:

*Leaf arrangement.*—Opposite.

*Leaf size.*—Lamina. Average length: 9.5 cm (range 8.5-10.5 cm; n=25). Average width: 5.6 cm (range 4.0-8.0 cm, n=25), the widest point being a little more than half-way down from the tip. Petiole: Average length 6.0 mm (range 4-10 mm, n=25).

*Shape.*—Ovate/elliptic. Tip: Acuminate. Base: Rounded. Number of pairs of veins: 5 to 6. Margin: Young, developing leaves have entire margins. Mature leaves become moderately undulate with some leaves slightly folded towards the adaxial side along the midvein.

*Texture.*—Adaxial surface is glabrous. The abaxial surface has slight pubescence due to presence of very tiny trichomes on the blade and tufts of longer trichomes in clumps along the midrib and the secondary veins.

*Coloration.*—Solid.

*Mature leaf color.*—Adaxial: Primarily the 137A and 137B Green Group. The color of the lower half of the mid vein on the adaxial side is between 59A and 59B of the Red Purple group. Abaxial: Primarily the 138B Green Group. The color of the mid vein on the abaxial side is 160C Greyed Yellow group with secondary veins 59B Red Purple Group. Petiole: Closest to 59B Red Purple group.

*Fall foliage (mid-October), New Brunswick, New Jersey.*—Adaxial surface: from a distance the color is primarily 187A and 187B Greyed-Purple group but up close the leaves are a mix of 137A Green Group, 187A Greyed-Purple Groups, 183A Greyed-Purple Group, 53A Red Group, and 46A Red Group. Abaxial surface: 138A Green Group. Leaf color can vary based on multiple environmental factors that includes soil type, presence of shade, air temperature, and water and nutrient availability. Thus, leaf color may vary from year to year and location.

Inflorescence:

*Location where observations were made.*—East Brunswick, New Jersey. Type of inflorescence: Flower head. Dense, rounded mound. Peduncle size (late May at time of anthesis): Average length (n=10): 7.0 cm (range=6.1 cm to 8.6 cm). Average width (n=10): 1.2 mm (range=1.0 mm-1.5 mm).

Floral bracts:

*Number.*—Four (two opposing pairs, lower and upper).

*Size of floral bracts at time of floral period late May to early June.*—.

*Lower floral bract dimensions.*—Average length 5.2 cm, n=20; average width 4.3 cm, n=20; and involucral spread 10.3 cm, n=10.

*Upper floral bract dimensions.*—Average length 4.9 cm, n=20; average width 4.2 cm, n=20; and involucral spread 9.8 cm, n=10. 'Rutglow' individual lower and upper floral bracts are similar in size and shape, with the lower bracts being just very slightly larger on average. Bract length and width will vary slightly from year-to-year based on environmental conditions and flower head numbers within the tree canopy, but the relationship between the size of the upper and lower bracts and the ratio of length to width across all bracts remains consistent.

*Shape.*—The individual floral bracts are rounded, acuminate at their tip, and obtuse at their base. The individual floral bracts overlap their adjacent partner bract at their bases over 50% of their total width at anthesis giving a symmetrical appearance to the complete floral bract structure. Younger bracts show overlap soon after development. The nearly symmetrical, overlapping bracts are a distinctive feature of 'Rutglow'.

*Color.*—At peak of floral display (approximately May 28 to June 2 in East Brunswick, New Jersey) in full sun exposure: Adaxial: Closest to 52A and 52B Red Group. Abaxial: Closest to 51B Red Group. Peduncle of floral structure is 144B Yellow Green group. Floral bract color lightens (55B Red Group) after anthesis and prior to dropping of the bracts, which occurs around June 15 in New Jersey.

*Flower description.*—Highly floriferous. Single flowers arranged in compact, dense heads subtended by the large floral bracts. The average number of true flowers per flower head is 40, ranging from 30 to 50 (n=10). No observed fragrance. Flowers are not persistent. Floral display of the involucral bracts typically lasts about six weeks depending on weather conditions.

*Flowering habit.*—Anthesis of the tiny, relatively inconspicuous true flowers generally begins around the time of peak ornamental display of the floral bracts (approximately May 28 to June 2 in East Brunswick, New Jersey).

Reproductive organs:

*Stamens per flower.*—4.

*Filament.*—Length: approximately 2.0 mm (n=5). Width: approximately 0.2 mm (n=5). Color: 155B White Group.

*Anther.*—Length: approximately 0.5 mm (n=5). Width: approximately 1.0 mm (n=4). Color: 162B Greyed-Yellow Group.

*Pollen.*—Color of freshly dehisced pollen is approximately 11C Yellow Group.

*Style.*—Height: approximately 1.0 mm (n=5). Width: approximately 0.3 mm (n=4). Color: 144C Yellow-Green Group.

*Stigma.*—Height: approximately 0.5 mm (n=5). Width: approximately 0.5 mm (n=5). Color: 144C Yellow-Green Group. All figures are based on an average of 5 measurements.

Fruit: Flower head with mature fruit. Fruits are 2-celled, typically 1-seeded, fleshy drupes that form a mounded, raspberry-like syncarp averaging 20 mm in length, 19 mm in width, and 17 mm in height (n=20). The multiple ovaries are enclosed in a fleshy, rounded mass typical for fruit of *Cornus kousa.* The exterior of the fruit is smooth except for the dried floral parts at the tip of each individual drupe. Fruit color varies from green to yellow to orange to red as the fruit matures and finally to 46A to 42C Red Group. Fruits ripen in September and can persist for around 6 weeks.

*Seed.*—Color when dry: Closest to 165C to 165D Greyed Orange Group. Size: Average 5 mm length, 4 mm width, and 4 mm in thickness (n=10). Shape: typical for *Cornus kousa.* Average number of seeds per fruit is 5 (n=10).

What is claimed is:

1. A new and distinct cultivar dogwood tree named 'Rutglow', substantially as herein shown and described, comprising an advanced generation seedling of *Cornus kousa* with overlapping, dark-pink colored floral bracts and attractive dark green foliage.

* * * * *